(12) United States Patent
Conway et al.

(10) Patent No.: US 11,145,412 B2
(45) Date of Patent: Oct. 12, 2021

(54) METHODS FOR THE DIAGNOSIS AND PROGNOSIS OF MELANOMA FROM TOPICAL SKIN SWABS

(71) Applicant: International Business Machines Corporation, Armonk, NY (US)

(72) Inventors: Thomas C. Conway, Heidelberg West (AU); Ismael A. Vergara Correa, Macleod (AU)

(73) Assignee: International Business Machines Corporation, Armonk, NY (US)

( * ) Notice: Subject to any disclaimer, the term of this patent is extended or adjusted under 35 U.S.C. 154(b) by 778 days.

(21) Appl. No.: 15/644,070

(22) Filed: Jul. 7, 2017

(65) Prior Publication Data

US 2019/0012433 A1    Jan. 10, 2019

(51) Int. Cl.
| | |
|---|---|
| *G16H 50/20* | (2018.01) |
| *G06N 5/04* | (2006.01) |
| *A61B 5/00* | (2006.01) |
| *A61B 10/02* | (2006.01) |
| *G16H 10/60* | (2018.01) |
| *G06N 20/00* | (2019.01) |
| *G06N 7/00* | (2006.01) |
| *G06N 20/10* | (2019.01) |
| *G06N 3/08* | (2006.01) |

(Continued)

(52) U.S. Cl.
CPC ............ *G16H 50/20* (2018.01); *A61B 5/444* (2013.01); *A61B 10/02* (2013.01); *G06N 5/04* (2013.01); *G06N 20/00* (2019.01); *G16H 10/60* (2018.01); *G06N 3/0454* (2013.01); *G06N 3/084* (2013.01); *G06N 7/005* (2013.01); *G06N 20/10* (2019.01); *G16H 50/70* (2018.01)

(58) Field of Classification Search
CPC ........ G16H 50/20; G16H 10/60; G16H 50/70; G06N 20/00; G06N 5/04; G06N 7/005; G06N 20/10; G06N 3/084; G06N 3/0454; A61B 5/444; A61B 10/02; G06F 19/30; G06F 19/32; G06F 19/34; G06F 19/36; G06Q 50/22; G06Q 50/24
See application file for complete search history.

(56) References Cited

U.S. PATENT DOCUMENTS

2016/0122806 A1* 5/2016 Amini .............. G01N 33/56911
514/789

OTHER PUBLICATIONS

L.C. Paulino et al., "Molecular Analysis of Fungal Microbiota in Samples from Healthy Human Skin and Psoriatic Lesions," Journal of Clinical Microbiology, Aug. 2006, pp. 2933-2941, vol. 44, No. 8.
(Continued)

*Primary Examiner* — Jesse P Frumkin
(74) *Attorney, Agent, or Firm* — Joseph Petrokaitis; Ryan, Mason & Lewis, LLP

(57) ABSTRACT

A method for predicting the presence of melanoma comprises performing molecular profiling of at least one of genomic and transcriptomic material extracted from a skin swab sample collected from a lesion of a patient, extracting one or more biological features from the molecular profiling, comparing the one or more extracted biological features to one or more biological features corresponding to one or more reference skin swab samples collected from a plurality of reference patients, and predicting, based on the comparing, whether the lesion of the patient is cancerous.

18 Claims, 6 Drawing Sheets

(51) Int. Cl.
G06N 3/04 (2006.01)
G16H 50/70 (2018.01)

(56) References Cited

OTHER PUBLICATIONS

O. Forslund et al., "High Prevalence of Cutaneous Human Papillomavirus DNA on the Top of Skin Tumors But Not in "Stripped" Biopsies from the Same Tumors," Journal for Investigative Dermatology, Aug. 2004, pp. 388-394, vol. 123, No. 2.
N. Fierer et al., "Forensic Identification Using Skin Bacterial Communities," Proceedings of the National Academy of Sciences (PNAS), Apr. 2010, pp. 6477-6481, vol. 107, No. 14.
E.A. Grice et al., "A Diversity Profile of the Human Skin Microbiota," Genome Research, Jul. 2008, pp. 1043-1050, vol. 18, No. 7.
F. Meyer et al., "The Metagenomics RAST Server—a Public Resource for the Automatic Phylogenetic and Functional Analysis of Metagenomes," BioMed Central (BMC) Bioinformatics, Sep. 2008, 8 pages, vol. 9.
R. Wong et al., "Use of RT-PCR and DNA Microarrays to Characterize RNA Recovered by Non-Invasive Tape Harvesting of Normal and Inflamed Skin," Journal for Investigative Dermatology, Jul. 2004, , pp. 159-167, vol. 123, No. 1.
A. Salava et al., "Skin Microbiome in Melanomas and Melanocytic Nevi," European Journal of Dermatology (EJD), Jan.-Feb. 2016, pp. 49-55, vol. 26, No. 1.

\* cited by examiner

METHODS FOR THE DIAGNOSIS AND PROGNOSIS OF MELANOMA FROM TOPICAL SKIN SWABS

BACKGROUND

Melanoma is a form of cancer with a large burden in many countries. Estimates from the American Cancer Society indicate that in the United States alone 87,110 new melanoma cases will be diagnosed and 9,730 people will die of this disease in 2017. While melanoma can be a fatal disease, it can be effectively treated when detected early, by for example, an excisional biopsy.

Typically, early detection of melanoma in a skin mole or other lesion is assessed by the presence/absence of certain features in the mole or other lesion. These examinations are usually formed as defined protocols used by health care professionals. For example, a health care professional may inspect suspect patches on the skin, and excise and test spots that appear to be potentially cancerous based on the defined protocols. Common features across these different protocols can include the presence of certain "colors" (brown, black, red, etc.) and/or patterns (networks, globules, etc.). This process to determine whether to perform a biopsy relies on the subjective judgment of health care professionals, which can result in unnecessary patient discomfort and expense to excise benign spots, or a failure to detect cancerous lesions. Further, conventional detection techniques may also lead to false positive or false negative results.

SUMMARY

According to an exemplary embodiment of the present invention, a method for predicting the presence of melanoma comprises performing molecular profiling of at least one of genomic and transcriptomic material extracted from a skin swab sample collected from a lesion of a patient, extracting one or more biological features from the molecular profiling, comparing the one or more extracted biological features to one or more biological features corresponding to one or more reference skin swab samples collected from a plurality of reference patients, and predicting, based on the comparing, whether the lesion of the patient is cancerous.

According to an exemplary embodiment of the present invention, a system for predicting the presence of melanoma comprises a memory and at least one processor coupled to the memory, wherein the at least one processor is configured to perform molecular profiling of at least one of genomic and transcriptomic material extracted from a skin swab sample collected from a lesion of a patient, extract one or more biological features from the molecular profiling, compare the one or more extracted biological features to one or more biological features corresponding to one or more reference skin swab samples collected from a plurality of reference patients, and predict, based on the comparison, whether the lesion of the patient is cancerous.

According to an exemplary embodiment of the present invention, a computer program product for predicting the presence of melanoma comprises a computer readable storage medium having program instructions embodied therewith, the program instructions executable by a processor to cause the processor to perform a method comprising performing molecular profiling of at least one of genomic and transcriptomic material extracted from a skin swab sample collected from a lesion of a patient, extracting one or more biological features from the molecular profiling, comparing the one or more extracted biological features to one or more biological features corresponding to one or more reference skin swab samples collected from a plurality of reference patients, and predicting, based on the comparing, whether the lesion of the patient is cancerous.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION

Exemplary embodiments of the invention will now be discussed in further detail with regard to diagnosis and prognosis of melanoma and, in particular, to using data from skin metagenomes to predict whether a lesion is benign or malignant. This invention may, however, be embodied in many different forms and should not be construed as limited to the embodiments set forth herein.

Embodiments of the current invention disclose a method for diagnostic and prognostic characterization of melanoma that involves: (i) collection of one or more samples from the skin using swabs; (ii) molecular profiling (e.g. by DNA sequencing) of the extracted genomic or transcriptomic material; and (iii) assessment of differential molecular signatures that produce a diagnostic or prognostic score associated to the risk of melanoma from the sample(s).

Figure 1:
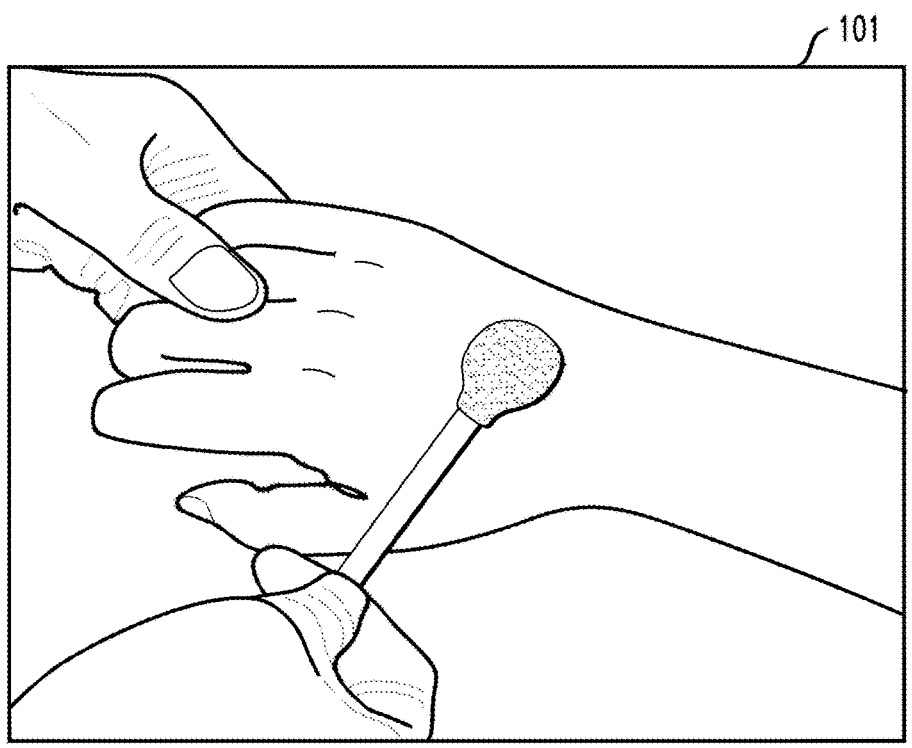
FIGS. 1 and 2 illustrate skin swabbing, according to an exemplary embodiments of the present invention.
Figure 2:
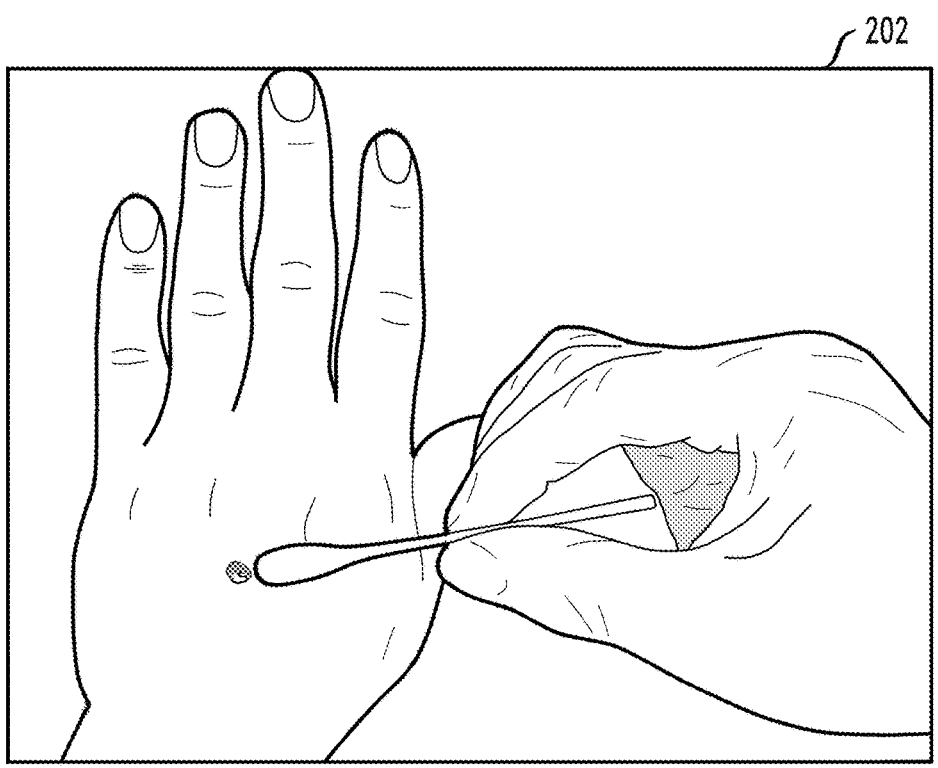

Referring generally to FIGS. 1 and 2, swabbing of the skin is a relatively non-invasive, painless and simple procedure, and hence an appealing method for sample collection in candidate regions indicative of melanoma. In general, bacteria living on the skin of humans will exhibit differences between skin swab samples taken from healthy skin and skin swab samples taken from cancerous lesions. Molecular profiling of the bacteria in the samples based on sequencing provides relatively high resolution for modest cost, and can be done relatively quickly. Accordingly, embodiments of the present invention utilize skin swabbing and sequencing to provide objective assessments of potential melanomas.

As used herein, "DNA sequencing" can refer to the process to determine the precise order of nucleotides within a DNA molecule, including methods or technology used to determine the order of the four bases in a strand of DNA, which are adenine, guanine, cytosine, and thymine. Sequencing can be used in several ways, including to read the genome from a purified sample of a single organism, the metagenome from a sample containing a collection of organisms, and the expressed transcriptome from a sample.

According to an embodiment of the present invention, skin swabs are collected from a population of patients that are candidates for melanoma diagnosis or prognosis. Each of these patients will be monitored in order to determine clinically the outcome in their case, including, for example, determinations that lesions are benign or malignant, and/or whether metastasis occurs. Samples can be labelled according to outcome (e.g. benign versus malignant and/or metastasis versus non-metastasis). The swabs can be stored and processed using methods known by those skilled in the art in order to obtain genomic and/or transcriptomic material of interest.

In a non-limiting illustrative example, in order to sample microbial communities from the skin, swabs can be obtained using a sterile cotton pledget soaked in sterile 0.15 M NaCl with 0.1% Tween® 20 nonionic detergent and wrung of excess solution. A sterile solution of 0.15 M NaCl is formed by dissolving 8.775 grams of NaCl per one liter of water. In this example, the amount of NaCl to be dissolved in one liter of water is determined by the equation 0.15 moles×58.5 grams/mole=8.775 grams, where the grams/mole of NaCl is 23 (Na)+35.5 (Cl))=58.5. Tween® 20 is a trademarked name for a series of non-ionic surfactants derived from sorbitan esters, known as polysorbate surfactants.

The swab (e.g., a cotton-tipped swab) can be rolled on a lesion (e.g., within margins of the lesion) in order to transfer part of the microbial community (e.g., bacteria) onto the swab, and suspended in 1 mL of saline. From each patient, samples of microbial communities from the skin can also be collected from, for example, healthy perilesional skin, forehead skin and buttock skin, by swabs, drawn to and from multiple times (e.g., 15 times) within a designated area (e.g., 5×5 cm), and suspended in 1 mL of saline. Swabs can then be stored at a predetermined temperature (e.g., −80° C.) before DNA extraction.

Genomic DNA can be extracted from the swabs into, for example, sample tubes, using an isolation kit, including, but not necessarily limited to, a PowerSoil® DNA isolation kit, available from MO BIO Laboratories, Inc. of West Carlsbad, Calif. The isolation kit isolates microbial genomic DNA from the skin samples. Cotton tips of frozen swabs can be broken off directly into bead tubes that contain a predetermined amount of aqueous lysis solution (e.g., 60 µL of PowerSoil® Solution C1, available from MO BIO Laboratories, Inc.). Tubes can then be incubated at a specified temperature for a specified time (e.g., 65° C. for 10 min) and then shaken. For example, when the PowerSoil® DNA isolation kit is used, the tubes can be shaken horizontally at maximum speed for 2 min using a vortex adapter, available from MO BIO Laboratories, Inc. Remaining steps can be performed as directed by a manufacturer of an isolation kit in order to extract the DNA and/or RNA from the samples.

Once DNA and/or RNA is extracted from a skin sample following standard methods, it is processed in a sequencer, such as, but not necessarily limited to, an Illumina® GA or Illumina® HiSeq sequencer available from Illumina, Inc. of San Diego, Calif., a Roche® 454 FLX sequencer, available from Hoffmann-La Roche Inc. of Nutley, N.J., or MinION® sequencing machine, available from Oxford Nanopore Technologies of Oxford, United Kingdom. The resulting FASTQ format computer files containing reads, represent the DNA and/or RNA content from each sample. "FASTQ format" refers to a text-based format for storing a biological sequence (e.g., nucleotide sequence) and its corresponding quality scores.

In accordance with an embodiment of the present invention, the set of samples is randomly divided into a training set and a validation set. The training set is used to train machine learning algorithms such as, but not necessarily limited to, a Support Vector Machine (SVM), a Multilayer Perceptron (MLP), a deep learning model and/or a neural network. The validation set is used to independently assess the performance of a generated classifier. The training data set includes samples which have labeled as, for example, benign or malignant. Machine learning is performed on the training set to build a prediction model that is used to clinically determine whether swabbed lesions are melanoma.

SVMs include supervised learning models with associated learning algorithms that analyze data used for classification and regression analysis. Given a set of training examples, each marked as belonging to one of a plurality of categories, an SVM training algorithm builds a model that assigns new examples to a particular category or the other. For example, for a linearly separable set of two-dimensional points which belong to one of two classes, given labeled training data (e.g., supervised learning), an SVM outputs an optimal hyperplane which categorizes new examples. An MLP is a supervised learning algorithm that learns a function by training on a dataset, where there is a number of input dimensions and a number of output dimensions. Given a set of features and a target, the MLP learns a non-linear function approximator for either classification or regression. Between the input and the output layer, there can be one or more non-linear layers, called hidden layers. The MLP maps sets of input data onto a set of appropriate outputs. The MLP includes multiple layers of nodes in a directed graph, with each layer fully connected to the next one. A neural network can refer to a feed-forward artificial neural network used in machine learning in which the connectivity pattern between its neurons are arranged in a particular way that they can mathematically be described. For example, the connectivity pattern between neurons of a convolutional neural network (CNN) is arranged in such a way that they can mathematically be described by a convolution operation.

In accordance with an embodiment of the present invention, after sequencing and appropriate filtering for low quality and other relevant controls, the reads associated to each sample are computationally processed for detection of differences between the malignant and benign groups, or metastasis and non-metastasis groups. In other words, feature extraction is performed to determine variants, k-mers and/or other features (e.g., DNA features) associated with the sequences. K-mers refer to all the possible subsequences (of length k) from a read obtained through DNA sequencing. Variants can be determined by comparing sequence data from a sequencer against reference sequences (e.g., from a benign or malignant lesion) to determine whether there are any mismatches, and determining whether the mismatches are sequencing errors or true mismatches. The extracted features are fed into a machine learning classifier, such as an SVM, MLP, deep learning model and/or neural network, which determines whether a sample lesion is malignant or benign.

In the case of DNA sequencing, the differences between the malignant and benign groups may be variants such as single nucleotide variants (SNVs), small InDels (insertion or deletion of bases in DNA of an organism) or larger structural variations, such as, but not necessarily limited to, inversions or reciprocal translocations in the case of human cells, and/or the presence versus absence and/or a certain population of microbial species/genus. For the latter, tools like a metagenomics rapid annotation using subsystem technology (MG-RAST) server can be used to determine differences of microbial populations from sequencing data. MG-RAST is a software engineering for educational development program (SEED) based environment that allows users to upload metagenomes for automated analyses. RAST technology allows automated high-quality annotation of complete or draft microbial genomes using SEED data and has been adapted for metagenome analysis. The server can provide the annotation of sequence fragments, their phylogenetic classification, functional classification of samples, and comparison between multiple metagenomes. The server can also compute an initial metabolic reconstruction for a metagenome and allows comparison of metabolic reconstructions of metagenomes and genomes.

In the case of RNA sequencing, and using the training set defined above, fold change (i.e., the ratio of median or mean expression between two groups of patients) can be measured between the malignant and benign groups, or metastasis and non-metastasis groups. In accordance with an embodiment of the present invention, those transcripts with a fold change greater than a certain threshold (e.g., ≥2-fold change) and a Wilcoxon p-value (probability value) (or a value from another statistical hypothesis test) paired with correction for multiple testing for the difference of the distribution between the two groups for a given transcript can be used as initial filters for selection of relevant transcripts, hereafter referred to as "markers." Methods, including, but not necessarily limited to, Benjamini Hochberg or other methods for decreasing false-discovery rate (FDR) can be used for correction for multiple testing for the difference of the distribution between the two or more groups.

Each marker can be then independently evaluated for its performance as a diagnostic and/or prognostic classifier for melanoma. From the training set, an optimal expression value threshold can be devised (e.g., by maximizing accuracy) and then used on the independent validation set to determine different performance metrics including accuracy, negative and positive predictive value, and area under the receiver operating characteristic (ROC) curve (AUC). "Diagnosis" or "diagnostic" can refer to the identification and understanding of the nature of a disease or disorder, and "prognosis" or "prognostic" can refer to a prediction of the probable outcome of a disease or disorder.

Additionally, in accordance with embodiments of the present invention, multivariate classifiers that combine two or more previously selected markers can be generated using machine learning algorithms such as, but not necessarily limited to, MLPs, SVMs and Bayesian networks, among others. Depending on the machine learning algorithm, the training set might need to be further split into a smaller training set and a control set to avoid over fitting of the generated classifier to the training set (e.g., the parameters associated to the backpropagation algorithm inherent in the MLP). Machine learning algorithms also have parameters that need to be tuned/optimized (e.g., learning rate, momentum and/or number of hidden layers and nodes per layer in MLPs, cost of error for soft margins in SVMs or the different search space algorithms for optimizing the structure of a Bayesian network) for which a validation approach such as, but not necessarily limited to, k-fold cross validation or leave-one-out cross validation, can be applied on the training set.

The generated classifier may yield a score (e.g., between 0 and 1 in the case of a probability) of the sample belonging to one class or the other (e.g. benign versus malignant, or metastasis versus non-metastasis), and a rule for defining the correspondence of this score to a binary outcome needs to be devised (e.g., 0.5 as a threshold). The performance of the generated classifier can then be assessed on the independent validation set by labelling each sample according to the outcome. As with the univariate classifiers represented by each transcript, different performance metrics including, but not necessarily limited to, accuracy, negative and positive predictive value, and AUC can be used for this purpose. It is to be understood that embodiments of the present invention may perform analysis in connection with benign versus malignant, metastasis versus non-metastasis or other categories for which lesions or cancer may be classified.

Associated p-values for tests associated to these metrics, such as, but not necessarily limited to, the McNemar test for the error rate or the DeLong test for AUC, can be used to compare the statistical significance of the differences between each pair of univariate or multivariate classifiers.

Additionally, and if available, survival differences between groups of patients with different classifier outcomes based on time-to-event data (e.g., time to metastasis of melanoma or time to death) can be computed by using, for example, Kaplan Meier curves, or another type of estimator for each group. In this case, the statistical significance of the difference between both groups can be computed with a log-rank test statistic.

In accordance with an embodiment of the present invention, in order to determine whether a mole or other type of lesion is melanoma, one or more samples are non-invasively collected from the skin using swabs, followed by molecular profiling (e.g. DNA sequencing) of extracted genomic or transcriptomic material, and assessment of differential molecular signatures to produce a diagnostic or prognostic score associated to the risk of melanoma from the samples. Accordingly, skin metagenomics (e.g., data from skin metagenomes) is being used to predict whether a lesion is benign or malignant. The prediction is based on a p-value threshold (e.g., ≤0.05) and can include a confidence level.

Figure 3:
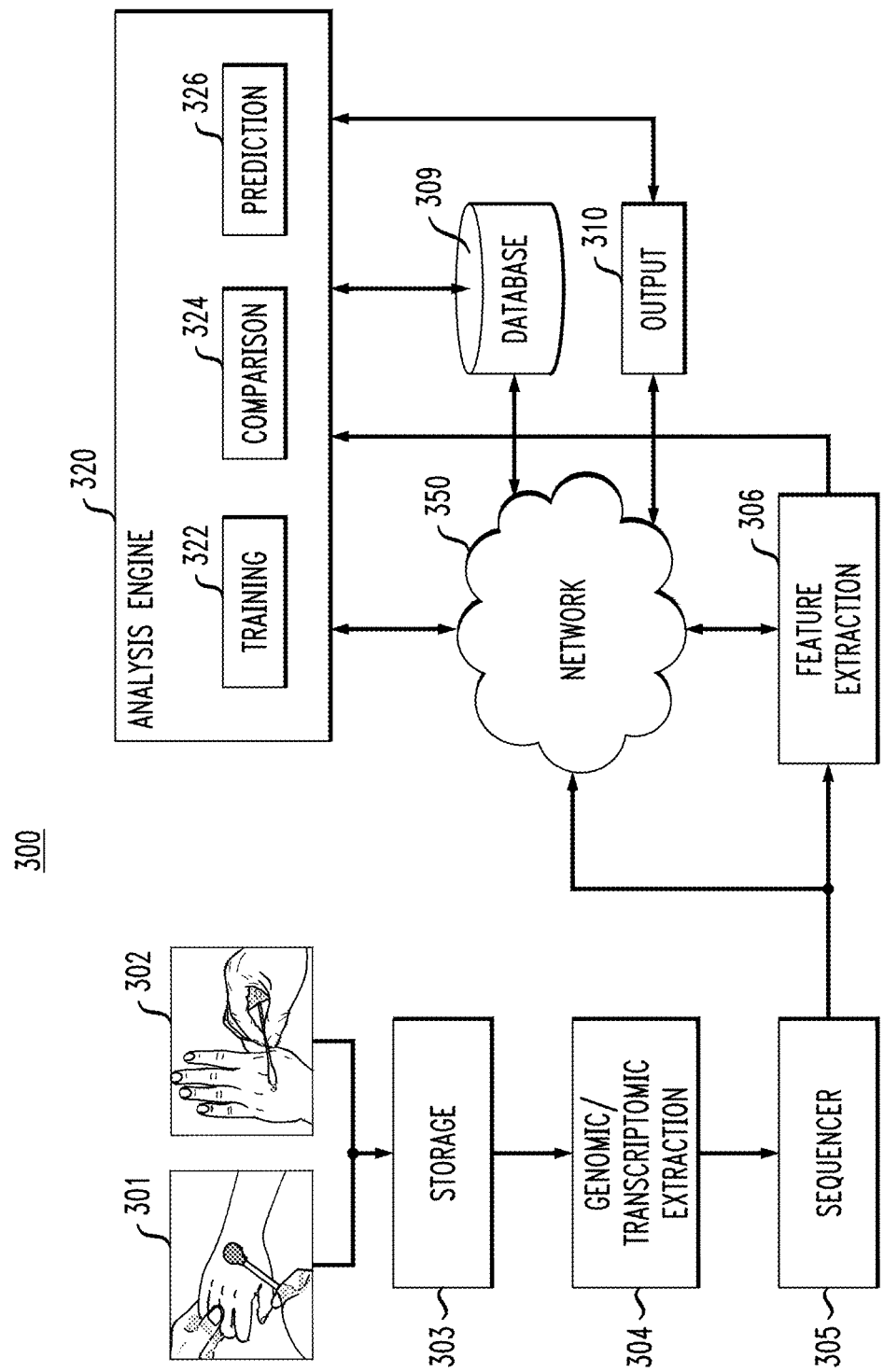
FIG. 3 is block diagram illustrating a system for diagnosis and prognosis of melanoma, according to an exemplary embodiment of the present invention.

FIG. 3 is block diagram illustrating a system for diagnosis and prognosis of melanoma, according to an exemplary embodiment of the present invention. As shown in FIG. 3 by lines and/or arrows, the components of the system 300 are operatively connected to each other via, for example, physical connections, such as wired and/or direct electrical contact connections, and/or wireless connections, such as, for example, WiFi, BLUETOOTH, IEEE 802.11, and/or networks, including but not limited to, a local area network (LAN), wide area network (WAN), cellular network, ad hoc networks, WANET, satellite network or the Internet. For example, a network 350 can operatively link components 305, 306, 309, 310 and 320 of the system 300.

By way of non-limiting example, in accordance with an embodiment of the present invention, referring to FIG. 3, the system includes a sequencer or other type of molecular profiling device that is used to perform molecular profiling (e.g., DNA and/or RNA sequencing) of genomic and/or transcriptomic material extracted from a skin swab sample 301, 302. The skin swab sample can be stored in storage 303. As noted above, the swab can be rolled on a lesion as shown in 302 in order to transfer part of a microbial community. Samples of microbial communities from the skin can also be collected as in 301 from, for example, healthy skin. Swabs with samples can be stored in storage at a predetermined temperature before extraction of genomic and/or transcriptomic material as in 304. As noted above, such extraction may be performed using an isolation kit.

Once genomic and/or transcriptomic material (e.g., DNA and/or RNA) is extracted from a skin, it is processed in a sequencer 305. Resulting computer files including, but not necessarily limited to, FASTQ format files, containing reads, represent the DNA and/or RNA content from each sample. In accordance with an embodiment of the present invention, after sequencing and appropriate filtering for low quality and other relevant controls, the reads associated to each sample are computationally processed by the analysis engine 320 for detection of differences between the malignant and benign groups, or metastasis and non-metastasis groups. A feature extraction engine 306 performs feature extraction to determine variants, k-mers and/or other features (e.g., DNA features) associated with the sequences. A comparison component 324 determines variants by comparing sequence data from a sequencer against reference sequences (e.g., from a known benign or malignant lesion), which can be stored in database 309, to determine whether there are any mismatches, and determine whether the mismatches are sequencing errors or true mismatches. The extracted features are transmitted to the analysis engine 320 from the feature extraction engine 306 directly or via network 350, where comparison and prediction components 324 and 326 use one or more machine learning classifiers, such as an SVM, MLP, deep learning model and/or neural network to determine whether a sample lesion is malignant or benign. The result of the analysis can be stored to database and output to user via an output component 310, and/or used by training component 322 to train a prediction model to determine whether future lesions are benign or malignant.

For example, the training component 322 uses a training set of the samples to train machine learning algorithms such as, but not necessarily limited to, an SVM, an MLP, a deep learning model and/or a neural network. The training component 322 uses a validation set of the samples to independently assess the performance of the generated classifier. Machine learning is performed on the training set to build the prediction model used by the prediction component 326 to clinically determine whether swabbed lesions are melanoma.

The database 309 can be used to store meta data and data associated with, for example, sequences, extracted features, analysis results and/or labels (e.g., benign or malignant) of skin samples that have been taken from of a plurality of patients. The analysis results stored in the database 309 can include, for example, determined variants or other variations, generated predictions and/or confidence levels. The database 309 can be, for example, cloud-based. The data from the database 309 are electronically accessible by the analysis engine 320 via the network 350 or directly. The database 309 is also configured to receive outputted data from the sequencing and feature extraction components 305 and 306 via network 350 or directly.

As noted herein, the analysis engine 320 evaluates skin sample sequence data to determine whether lesion(s) which are the subject of the skin samples are cancerous or will become cancerous. The analysis engine 320 communicates with and transmits information to one or more output devices 310 either directly or via a network 350 so that a specialist (e.g., skin cancer specialist), a patient, a non-expert practitioner (e.g., general practitioner) or other users with access to the system, can view the determinations made by the analysis engine 320 and decide on which actions to take for a patient. The output device 108 can include, for example, a desktop or portable computer, tablet, personal digital assistant (PDA), smart phone or other computing device having an interface for viewing the results, determinations or requests.

Figure 4:
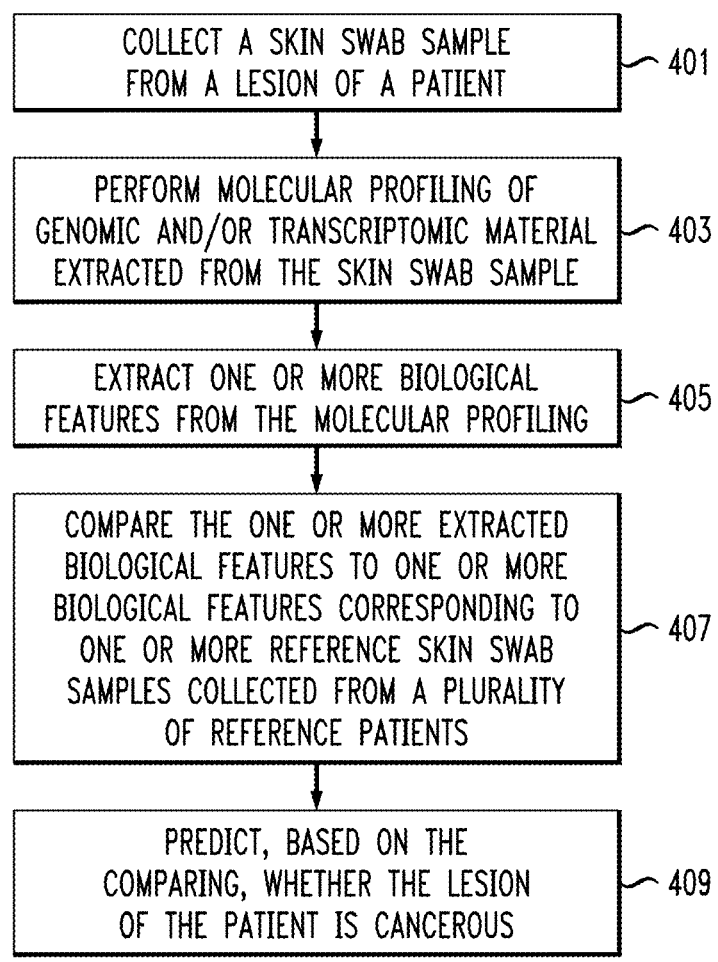
FIG. 4 is a flow diagram of a process for diagnosis and prognosis of melanoma, according to an exemplary embodiment of the invention.

FIG. 4 is a flow diagram of a process for diagnosis and prognosis of melanoma, according to an exemplary embodiment of the invention. Referring to FIG. 4, the process 400 includes, at block 401, collecting a skin swab sample from a lesion of a patient, from which genomic and/or transcriptomic material (e.g., DNA, RNA) can be extracted. Referring to block 403, molecular profiling of at least one of genomic and transcriptomic material extracted from the skin swab sample is performed using, for example, a sequencer. Computer files representing biological sequence data of the genomic and transcriptomic material (e.g., FASTQ files) can be generated.

Referring to block 405, one or more biological features (e.g., k-mers, variants, etc.) are extracted from the molecular profiling. At block 407, the one or more extracted biological features are compared to one or more biological features corresponding to one or more reference skin swab samples collected from a plurality of reference patients, and, at block 409, based on the comparing, a prediction is made whether the lesion of the patient is cancerous. The prediction is based on a p-value threshold, and can include a confidence level.

The comparing is performed using at least one machine learning-based algorithm that has been trained using the one or more reference skin swab samples collected from lesions and perilesional skin of the plurality of reference patients, wherein the one or more reference skin swab samples each have a known label, such as, for example benign or malignant.

In general, embodiments of the present invention utilize molecular profiling and machine learning to learn from labeled training samples differences between molecular signatures of microbial communities associated with skin samples from cancerous lesions and skin free of cancerous lesions. The learned differences can be compared with the molecular signature of a swabbed skin sample from a lesion of a patient to predict whether the lesion is benign or malignant.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 5:
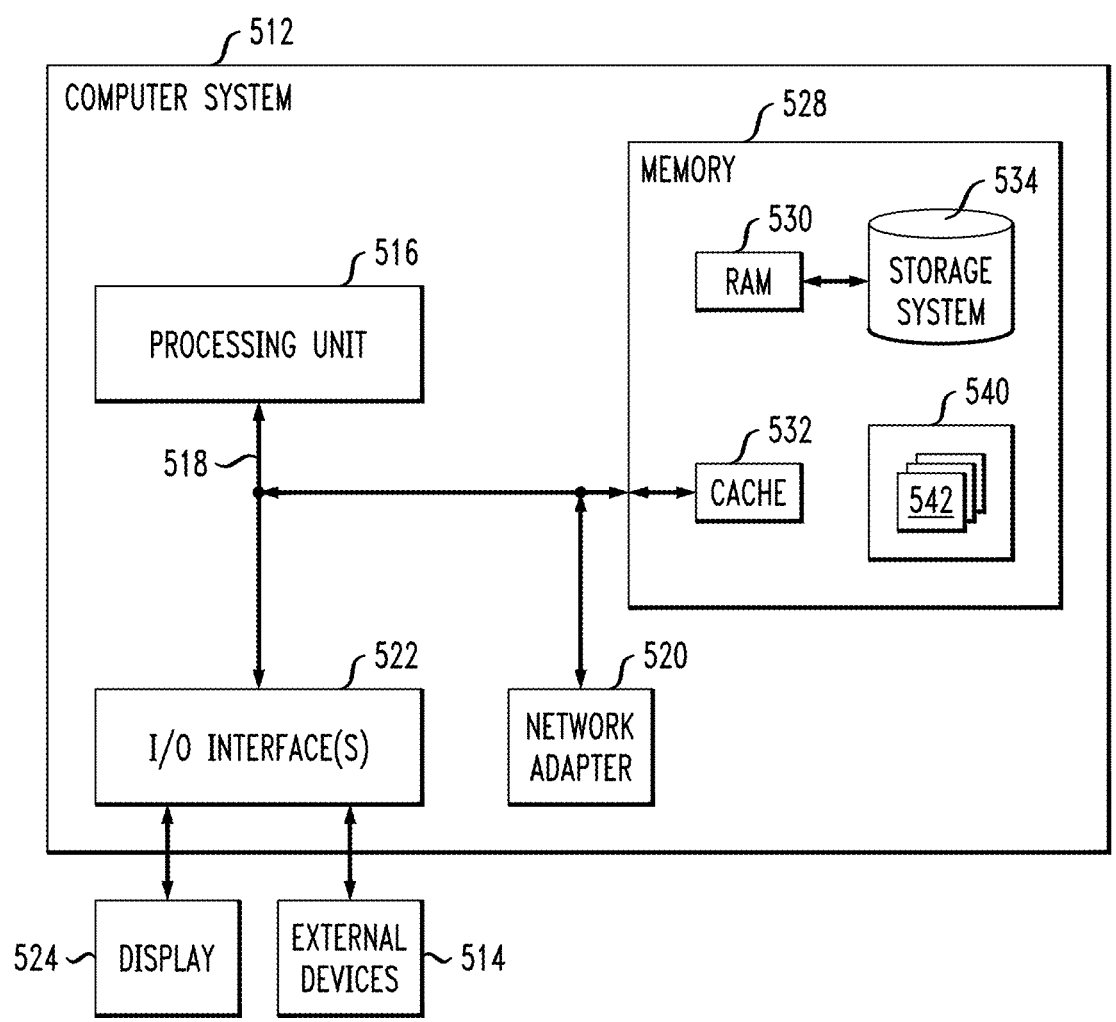
FIG. 5 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 5, in a computing node 510 there is a computer system/server 512, which is operational with numerous other general purpose or special purpose computing system environments or configurations. Examples of well-known computing systems, environments, and/or configurations that may be suitable for use with computer system/server 512 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 512 may be described in the general context of computer system executable instructions, such as program modules, being executed by a computer system. Generally, program modules may include routines, programs, objects, components, logic, data structures, and so on that perform particular tasks or implement particular abstract data types. Computer system/server 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 512 in computing node 510 is shown in the form of a general-purpose computing device. The components of computer system/server 512 may include, but are not limited to, one or more processors or processing units 516, a system memory 528, and a bus 518 that couples various system components including system memory 528 to processor 516.

The bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 512 typically includes a variety of computer system readable media. Such media may be any available media that is accessible by computer system/server 512, and it includes both volatile and non-volatile media, removable and non-removable media.

The system memory 528 can include computer system readable media in the form of volatile memory, such as random access memory (RAM) 530 and/or cache memory 532. The computer system/server 512 may further include other removable/non-removable, volatile/nonvolatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 518 by one or more data media interfaces. As depicted and described herein, the memory 528 may include at least one program product having a set (e.g., at least one) of program modules that are configured to carry out the functions of embodiments of the invention. A program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system/server 512 may also communicate with one or more external devices 514 such as a keyboard, a pointing device, a display 524, etc., one or more devices that enable a user to interact with computer system/server 512, and/or any devices (e.g., network card, modem, etc.) that enable computer system/server 512 to communicate with one or more other computing devices. Such communication can occur via Input/Output (I/O) interfaces 522. Still yet, computer system/server 512 can communicate with one or more networks such as a local area network (LAN), a general wide area network (WAN), and/or a public network (e.g., the Internet) via network adapter 520. As depicted, network adapter 520 communicates with the other components of computer system/server 512 via bus 518. It should be understood that although not shown, other hardware and/or software components could be used in conjunction with computer system/server 512. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 510 in FIG. 5 can be an example of a cloud computing node. Computing node 510 is only one example of a suitable cloud computing node and is not intended to suggest any limitation as to the scope of use or functionality of embodiments of the invention described herein. Regardless, computing node 510 is capable of being implemented and/or performing any of the functionality set forth hereinabove. It is also to be understood that computing node 510 is not necessarily a cloud computing node.

Figure 6:
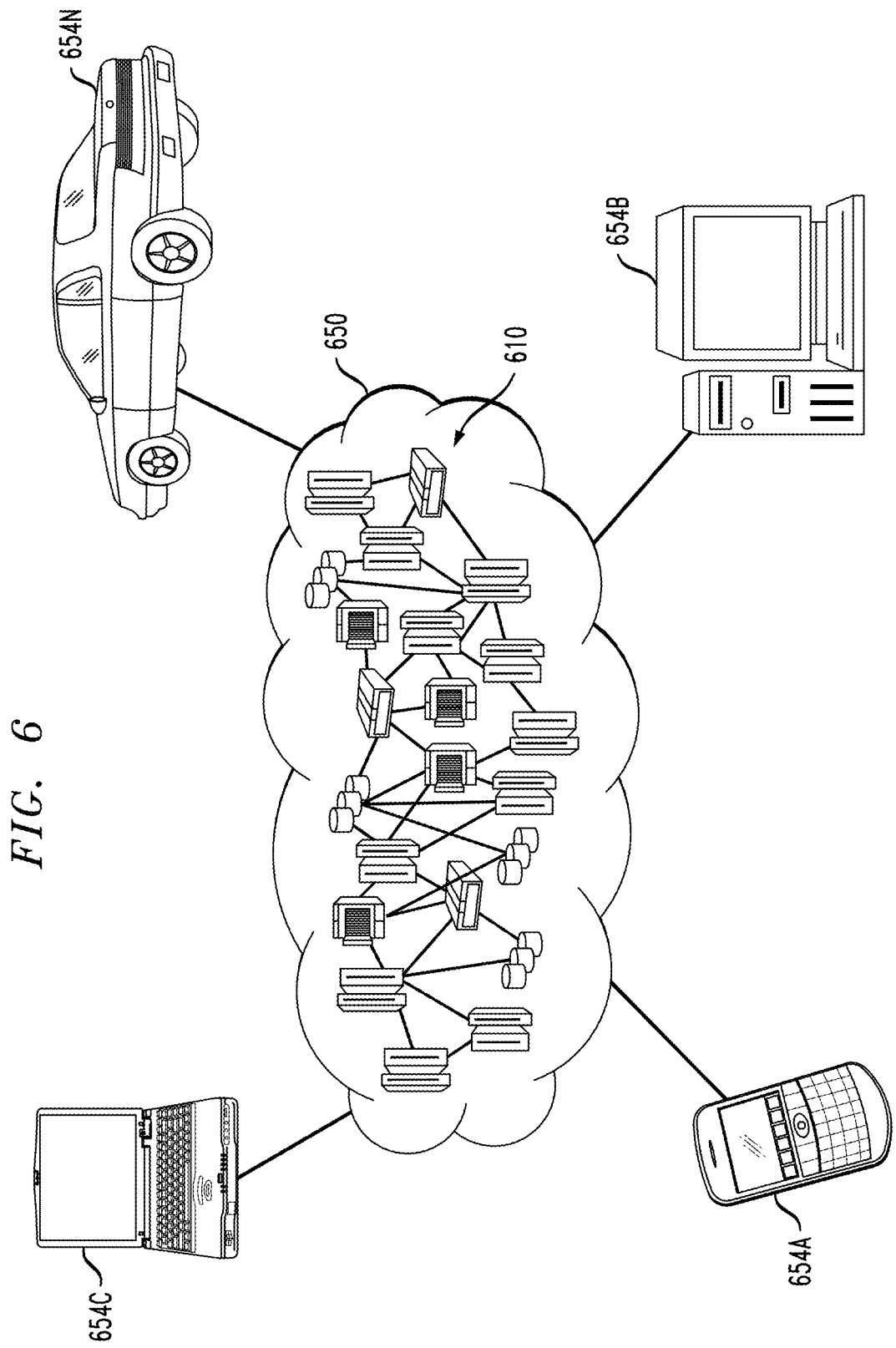
FIG. 6 depicts a cloud computing environment, according to an exemplary embodiment of the present invention.

Referring now to FIG. 6, illustrative cloud computing environment 650 is depicted. As shown, cloud computing environment 650 comprises one or more cloud computing nodes 610 with which local computing devices used by cloud consumers, such as, for example, a wearable device (not explicitly shown), a personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
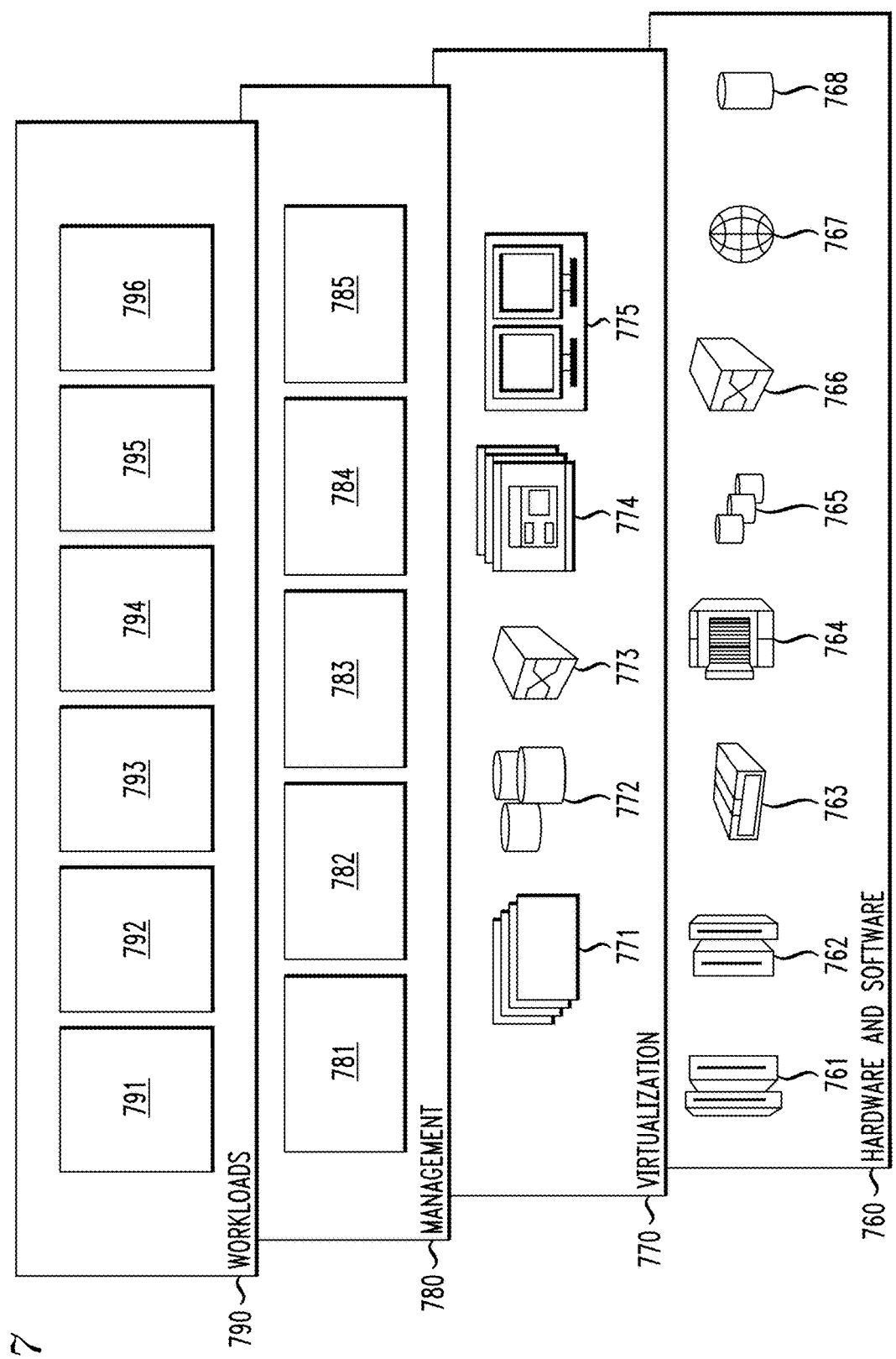
FIG. 7 depicts abstraction model layers, according to an exemplary embodiment of the invention.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and lesion analysis and disease diagnosis and prognosis 796, which may implement the functionality described above with respect to FIGS. 1-7.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for predicting the presence of melanoma, comprising:
   performing molecular profiling of at least one of genomic and transcriptomic material extracted from a skin swab sample collected from a lesion of a patient;
   wherein the performing of the molecular profiling comprises generating, with a sequencing machine, one or more computer files in a text-based format representing biological sequence data of the at least one of the genomic and transcriptomic material; and
   wherein the one or more computer files comprise at least one biological sequence;

extracting one or more biological features from the molecular profiling;

wherein the extracting comprises:

comparing the at least one biological sequence from the one or more computer files to a plurality of reference sequences to determine one or more differences between the at least one biological sequence and the plurality of reference sequences; and for at least one genomic material sample, inputting the at least one biological sequence from the one or more computer files to a rapid annotation component, and receiving one or more microbial population variances from the rapid annotation component;

wherein the plurality of reference sequences correspond to a plurality of reference skin swab samples collected from a plurality of reference patients; and evaluating, with a machine learning classifier, the one or more extracted biological features to generate a prognosis protocol comprising: (i) a score for the skin swab sample associated to a risk of cancer; (ii) a prediction whether the lesion of the patient is cancerous based at least in part on the score; and (iii) a computation of survival differences between groups of patients with different machine learning classifier outcomes;

wherein the evaluating comprises:

generating a prediction model from a training data set comprising biological sequence samples respectively corresponding to one or more known labels of one of a cancerous group and a non-cancerous group;

inputting the one or more differences and the one or more microbial population variances to the prediction model; and using the prediction model to generate the prognosis protocol including in part a determination whether the one or more differences and the one or more microbial population variances are indicative of cancer;

wherein the method is performed by at least one computer system comprising at least one memory and at least one processor coupled to the memory.

2. The method according to claim 1, wherein the at least one of the genomic and transcriptomic material comprises DNA.

3. The method according to claim 1, wherein the machine learning classifier uses at least one machine learning-based algorithm.

4. The method according to claim 3, wherein the training data set is derived from the plurality of reference skin swab samples, wherein the plurality of reference skin swab samples each correspond to the one or more known labels.

5. The method according to claim 4, wherein the one or more known labels comprise one of benign and malignant.

6. The method according to claim 3, wherein the machine learning classifier comprises at least one of a Support Vector Machine (SVM), a Multilayer Perceptron (MLP), a deep learning model and a neural network.

7. The method according to claim 1, wherein the training data set is derived from the plurality of reference skin swab samples and the plurality of reference skin swab samples are divided into the training data set and a validation data set.

8. The method according to claim 1, wherein the plurality of reference skin swab samples are collected from lesions and perilesional skin of the plurality of reference patients.

9. The method according to claim 1, wherein the one or more extracted biological features comprise at least one of a variant and a k-mer associated with the at least one biological sequence.

10. The method according to claim 9, wherein the variant comprises at least one of a single nucleotide variant and an InDel.

11. The method according to claim 9, wherein the variant comprises at least one of an inversion, a reciprocal translocation, and the one or more microbial population variances comprising the presence or absence of a population of a microbial species or genus.

12. The method according to claim 1, wherein the prediction whether the lesion of the patient is cancerous is based on a p-value threshold.

13. The method according to claim 1, wherein the prediction includes a confidence level.

14. A system for predicting the presence of melanoma, comprising:

a memory and at least one processor coupled to the memory, wherein the at least one processor is configured to:

perform molecular profiling of at least one of genomic and transcriptomic material extracted from a skin swab sample collected from a lesion of a patient;

wherein the performing of the molecular profiling comprises generating, with a sequencing machine, one or more computer files in a text-based format representing biological sequence data of the at least one of the genomic and transcriptomic material; and wherein the one or more computer files comprise at least one biological sequence;

extract one or more biological features from the molecular profiling;

wherein, in extracting, the at least one processor is configured to;

compare the at least one biological sequence from the one or more computer files to a plurality of reference sequences to determine one or more differences between the at least one biological sequence and the plurality of reference sequences; and for at least one genomic material sample, input the at least one biological sequence from the one or more computer files to a rapid annotation component, and receive one or more microbial population variances from the rapid annotation component;

wherein the plurality of reference sequences correspond to a plurality of reference skin swab samples collected from a plurality of reference patients; and evaluate, with a machine learning classifier, the one or more extracted biological features to generate a prognosis protocol comprising: (i) a score for the skin swab sample associated to a risk of cancer; (ii) a prediction whether the lesion of the patient is cancerous based at least in part on the score; and (iii) a computation of survival differences between groups of patients with different machine learning classifier outcomes;

wherein, in evaluating, the at least one processor is configured to:

generate a prediction model from a training data set comprising biological sequence samples respectively corresponding to one or more known labels of one of a cancerous group and a non-cancerous group;

input the one or more differences and the one or more microbial population variances to the prediction model; and use the prediction model to generate the prognosis protocol including in part a determination whether the one or more differences and the one or more microbial population variances are indicative of cancer.

15. The system according to claim 14, wherein the machine learning classifier uses at least one machine learning-based algorithm.

16. The system according to claim 15, wherein the training data set is derived from the plurality of reference skin swab samples, wherein the plurality of reference skin swab samples each correspond to the one or more known labels.

17. The system according to claim 15, wherein the one or more extracted biological features comprise at least one of a variant and a k-mer associated with the at least one biological sequence.

18. A computer program product for image analysis, the computer program product comprising a computer readable storage medium having program instructions embodied therewith, the program instructions executable by a processor to cause the processor to perform a method comprising:
  performing molecular profiling of at least one of genomic and transcriptomic material extracted from a skin swab sample collected from a lesion of a patient;
  wherein the performing of the molecular profiling comprises generating, with a sequencing machine, one or more computer files in a text-based format representing biological sequence data of the at least one of the genomic and transcriptomic material; and
  wherein the one or more computer files comprise at least one biological sequence;
  extracting one or more biological features from the molecular profiling;
  wherein the extracting comprises:
  comparing the at least one biological sequence from the one or more computer files to a plurality of reference sequences to determine one or more differences between the at least one biological sequence and the plurality of reference sequences; and
  for at least one genomic material sample, inputting the at least one biological sequence from the one or more computer files to a rapid annotation component, and receiving one or more microbial population variances from the rapid annotation component;
  wherein the plurality of reference sequences correspond to a plurality of reference skin swab samples collected from a plurality of reference patients; and
  evaluating, with a machine learning classifier, the one or more extracted biological features to generate a prognosis protocol comprising: (i) a score for the skin swab sample associated to a risk of cancer; (ii) a prediction whether the lesion of the patient is cancerous based at least in part on the score; and (iii) a computation of survival differences between groups of patients with different machine learning classifier outcomes;
  wherein the evaluating comprises:
    generating a prediction model from a training data set comprising biological sequence samples respectively corresponding to one or more known labels of one of a cancerous group and a non-cancerous group;
    inputting the one or more differences and the one or more microbial population variances to the prediction model; and
    using the prediction model to generate the prognosis protocol including in part a determination whether the one or more differences and the one or more microbial population variances are indicative of cancer.

* * * * *